United States Patent [19]

Dimarogonas

[11] Patent Number: 5,614,674
[45] Date of Patent: *Mar. 25, 1997

[54] METHOD AND APPARATUS FOR PREDICTING FATIGUE BY INTRODUCING A CONTINUOUS EXCITATION TO DETERMINE DAMPING FACTOR

[75] Inventor: Andrew D. Dimarogonas, St. Louis, Mo.

[73] Assignee: Washington University, St. Louis, Mo.

[ * ] Notice: The term of this patent shall not extend beyond the expiration date of Pat. No. 5,402,781.

[21] Appl. No.: 473,728

[22] Filed: Jun. 7, 1995

Related U.S. Application Data

[62] Division of Ser. No. 25,940, Mar. 3, 1993, Pat. No. 5,476,009.

[51] Int. Cl.⁶ .................................................. G01N 29/00
[52] U.S. Cl. ............................................. 73/577; 73/584
[58] Field of Search .......................... 73/577, 579, 582, 73/588, 862.59, 808, 82, 662, 593; 364/507, 508

[56] References Cited

U.S. PATENT DOCUMENTS

| | | | |
|---|---|---|---|
| 3,014,364 | 12/1961 | Crooks | 73/588 |
| 3,106,838 | 10/1963 | Crooks | 73/582 |
| 3,153,338 | 10/1964 | Kleesattel | 73/573 |
| 3,531,982 | 10/1970 | Clotfelter et al. | 73/582 |
| 3,744,299 | 7/1973 | Bliss | 73/595 |
| 3,857,279 | 12/1974 | Salzer | 73/582 |
| 4,031,744 | 6/1977 | Flannelly | 73/583 |
| 4,064,745 | 12/1977 | Gaddum | 73/805 |
| 4,297,884 | 11/1981 | Leveque et al. | 73/579 |
| 4,542,639 | 9/1985 | Cawley | 73/588 |
| 4,646,754 | 3/1987 | Seale | 128/774 |
| 4,705,146 | 11/1987 | Tarter | 73/579 |
| 4,854,172 | 8/1989 | Lemaster et al. | 73/587 |
| 4,918,616 | 4/1990 | Yoshimura et al. | 73/587 |
| 5,210,704 | 5/1993 | Husseiny | 364/506 |
| 5,305,645 | 4/1994 | Reifsnider et al. | 73/808 |
| 5,402,781 | 4/1995 | Dimarogonas | 73/579 |
| 5,476,009 | 12/1995 | Dimarogonas | 73/582 |

OTHER PUBLICATIONS

*The American Society of Mechanical Engineering* paper entitled *Structural Damping*, presented at a colloquium on structural damping held at the ASME annual meeting, pp. 1–34, Dec. 1959.

*Calcified Tissue International* article entitled *Material Damping for Monitoring of Density and Strength of Bones*, by Andrew D. Dimarogonas et al., 1993, 52:244–247.

*Primary Examiner*—Christine K. Oda
*Attorney, Agent, or Firm*—Howell & Haferkamp, L.C.

[57] ABSTRACT

The fatigue integrity of metallic materials may be determined by either one of two methods. In a first method, an impulse of energy is introduced into the material, such as by striking the material (20), and the induced vibration is sensed and analyzed in order to compute the damping factor thereof, the damping factor being directly related to the fatigue thereof. With this method, a transducer (28) is coupled to the material and its output is amplified by an amplifier (30) before input to a computer (32) which determines the damping factor. In a second method, a continuous energy input is provided to the material, such as by utilizing a frequency generator coupled to a power amplifier whose output drives a transducer such as a speaker or the like for inducing a continuous vibration in the metallic material. This continuous vibration is measured with a transducer, an amplifier, and a damping factor calculated with a computer as in the first method.

18 Claims, 2 Drawing Sheets

METHOD AND APPARATUS FOR PREDICTING FATIGUE BY INTRODUCING A CONTINUOUS EXCITATION TO DETERMINE DAMPING FACTOR

This is a divisional of application Ser. No. 08/025,940; filed on Mar. 3, 1993 U.S. Pat. No. 5,476,009.

BACKGROUND AND SUMMARY OF THE INVENTION

There are many-applications wherein metallic materials are used for their strength and endurance and are therefore subjected to loads, stresses, strains, and other forces which, over time, may have a tendency to fatigue the material and create a risk of catastrophic failure. It would be highly desirable to be able to test these discrete metallic parts in situ for their state of fatigue such that they might be replaced or renewed prior to any such catastrophic failure. In still other instances, and especially for critical applications involving health and safety, standards have been established for the routine testing of certain metallic parts prior to their being placed in service to ensure against any such failure of the part. In those applications, techniques have been developed and are available in the prior art to achieve such testing. These include such things as x-ray, destructive testing of selected parts from a lot, and other all techniques of these techniques being well known in the art. However these techniques are all subject to certain drawbacks such as expense, inconvenience, and in some cases failure to entirely eliminate the possibility of premature failure of the part. Still another situation in which these kinds of tests for fatigue are conducted involve many instances where materials or parts are welded and the integrity of the weld must be verified prior to the equipment being placed in service. One particular application, from amongst many, involves the federal safety standards which govern the construction of nuclear power plants. Certain welds in certain critical equipment contained within the plant are subjected to x-ray and other kinds of testing in order to verify their integrity prior to the plant being placed in service. A nuclear power plant presents perhaps an extreme example of the potential harm which might befall not only the people involved but the public at large should a critical piece of equipment suffer a premature failure. There are a myriad of other applications perhaps considered not as critical but which also are important to the health and safety of many people, including the public at large.

Despite the fact that testing for fatigue has been utilized for some time, and the relationship of damping to fatigue has been well known for some time, the inventor is not aware of any other efforts in the prior art to utilize the relationship of damping to fatigue in the arena of fatigue testing. For example, in a paper presented at a colloquium on structural damping at the ASME Annual Meeting in Atlantic City, N.J. in December of 1959, the phenomenon of "plastic strain" was analyzed. In particular, damping was used as a parameter for determining the interrelationship between stress history and stress amplitude as mechanisms for affecting plastic strain in a material. As concluded in the paper, at low stresses and intermediate stresses, within 1–50% of a fatigue limit, damping was not seen to be affected by the stress history of the material. On the other hand, at high stresses, typically above 50% fatigue limit, where large plastic strain damping may be observed, stress history played a part in affecting plastic strain, as measured by the damping factor. Stated differently, data were presented indicating that at low and intermediate stress, the damping factor does not change with the number of fatigue cycles. However, above a critical stress, damping increases with the number of fatigue cycles thereby indicating that stress history plays a part in plastic strain under these conditions. Although this article treated the interrelationship between stress history and stress amplitude, and their effect on damping (plastic strain), there was no disclosure or suggestion of utilizing a measured damping factor as an indicator of the state of fatigue of a material. As stated therein, the article focused on how stress history and amplitude might produce a particular damping factor but not how a measured damping factor could be used as a predictor of relative fatigue in a part. See *Structural Damping* edited by Jerome E. Ruzicka, ASME Proceedings, 1959.

In order to solve these and other problems in the prior art, and as a departure from the teachings in the prior art, the inventor herein has succeeded in developing the technique of measuring the damping factor of a discrete piece of metallic material, such as a part in an assembly or the like, and using that damping factor for determining the fatigue integrity of that part either by comparing it with a standardized damping factor or with previously measured damping factors for the same part. The part might be a single piece of material, or it might be a welded or otherwise joined piece of material and the test may be one for integrity, i.e. cracking, voids, or the like, as might be required for a new part, or the test might be conducted for determining the fatigue in the part after having been installed and used over time. For new part testing, it is anticipated that standardized damping factors may be determined and available for comparison with the measured damping factor for the new part. Alternately, the damping factor of a series of identical new parts might be measured and used to cull out those new parts which evidence signs of early fatigue and failure, or cracks, voids, or other defects in manufacture. After a part has been installed and used over a period of time, a damping factor measurement may be made periodically to determine the part's increasing fatigue. This technique may be used to identify parts which are in need of replacement prior to any chance of catastrophic failure. There are other applications and situations in which the damping factor measurement of a discrete piece of metallic material might be used to good advantage. These particular examples are being given as exemplary.

In making the damping factor measurement, the inventor herein has also succeeded in developing a simple but effective and accurate technique for measuring the damping factor using either of two methods. Utilizing a first method, an impulse of energy may be applied to the part, such as by striking it with a blunt object or the like, and the induced vibration in the part measured by a transducer which converts the vibration into an electrical signal for input to a computer. A computer may then easily make the appropriate calculation from the induced vibration to determine the damping factor. Generally, as is known in the art, the damping factor of a part vibrating at its natural frequency may be determined by comparing peak amplitudes of successive cycles of the vibration. In an alternative method, a continuous input of energy may be provided to the part instead of an impulse of energy. In a preferred embodiment, a frequency generator may be coupled to a transducer, such as a speaker, shaker, or other such device, and the frequency generator tuned or adjusted so as to sweep through the range of the lowest natural frequencies of the part. As the input of energy remains constant, the part would continue to vibrate at its natural frequency such that the damping factor may be readily calculated by measuring the half-power bandwidth of a cycle and dividing it by the center frequency, as is well known in the art. Using either of these methods, a vibration is induced in the part and the response thereto is measured from which the damping factor is determined.

One of the advantages of using the inventor's method of inducing a vibration in the part is that it is believed that the part need not be isolated and may be tested in place. This eliminates disassembly of the part from any larger assemblage which dramatically reduces any costs involved in using the present method in determining the damping factor. This provides great advantages over other prior art methods which require disassembly and isolation of the part to be tested, such as in the x-ray method. Furthermore, the device used to implement the method disclosed herein may be relatively compact, readily portable, and sufficiently small such that the testing of many differently sized parts which might be otherwise relatively difficult to access may be readily tested.

While the principal advantages and features of the present invention have been described above, a more complete and thorough understanding of the invention may be attained by referring to the drawings and description of the preferred embodiment which follow.

DETAILED DESCRIPTION OF THE PREFERRED EMBODIMENT

Figure 1:
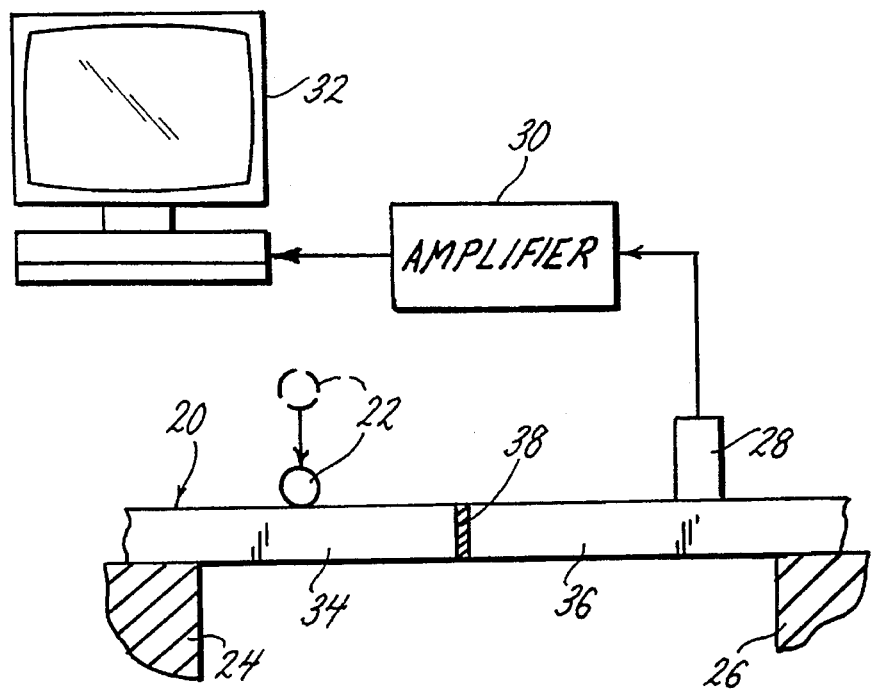
FIG. 1 is a diagrammatic view of the inventor's first technique for measuring material integrity utilizing an impulse of energy input to induce a vibration into the material.
Figure 2:
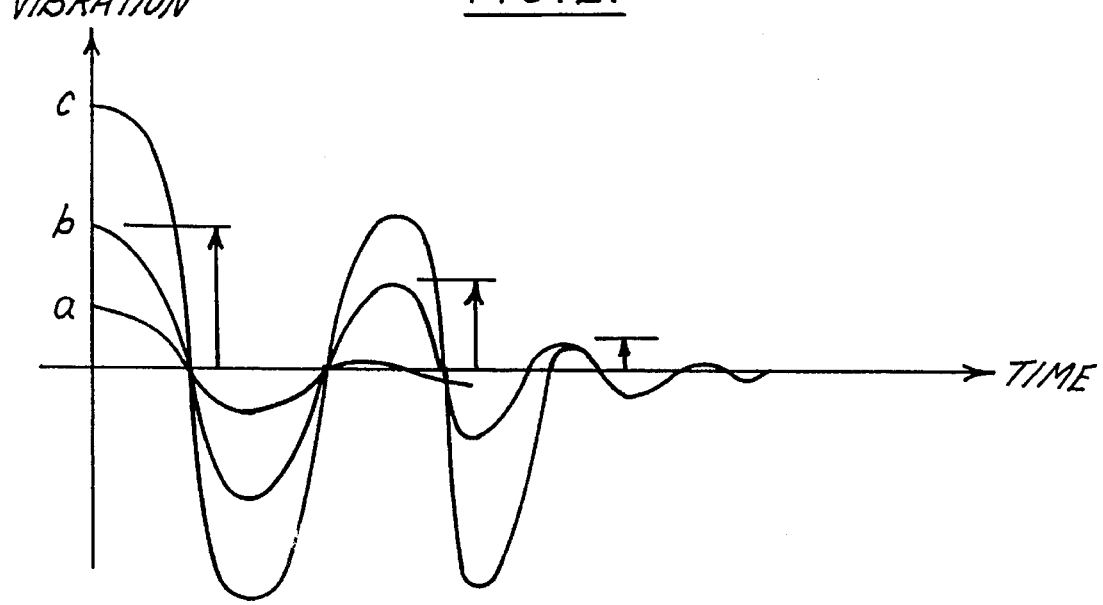
FIG. 2 is a graph of the harmonic response of vibrations induced in the material through the technique shown in FIG. 1.

As shown in FIGS. 1 and 2, the inventor's first technique for measuring relative fatigue in a part includes the step of inducing a vibration in the part desired to be measured, such as by striking the part 20 with a blunt instrument such as a rod 22 to thereby induce vibrations in the part 20. For convenience, the opposite ends of the part 20 may be supported by a pair of supports 24, 26, although this is not believed to be necessary. A transducer 28 measures the induced vibration and produces an electrical output which is amplified by an amplifier 30 and then input to a computer 32 for calculation of the damping factor. As shown in FIG. 2, the vibration induced by the input of an impulse of energy into the part 20 may have a varying amplitude or force level. The damping factor, as is well known, may be readily calculated by comparing the amplitudes of successive cycles of vibration induced by any one of these force levels. As shown in FIG. 2, the intensity of the blow to the part does not affect the measurement of the damping factor as the damping factor is determined by comparing two successive peak amplitudes, regardless of the size thereof. Whether the initial amplitude has an intensity of a, b, or c, there is no variation in the measured damping factor. Instead, the damping factor is determined solely by the characteristics of the part 20.

As shown in FIG. 1, the part 20 may in actual fact be comprised of a pair of elements 34, 36 which are joined by a weld 38 or the like. If that is the case, then the integrity of the weld 38 may be readily determined by the measurement of the damping factor. Similarly, the joint, shown in FIG. 1 as weld 38, may be any other joint or connection and its integrity similarly measured through the methodology disclosed herein.

Figure 3:
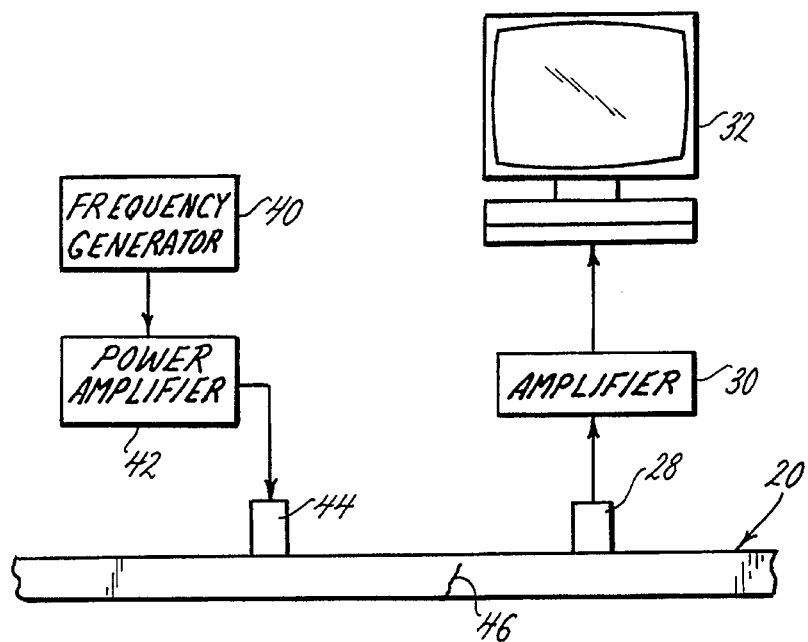
FIG. 3 is a diagrammatic view of the inventor's second technique for measuring material integrity through the coupling of a continuous energy source to the material.
Figure 4:
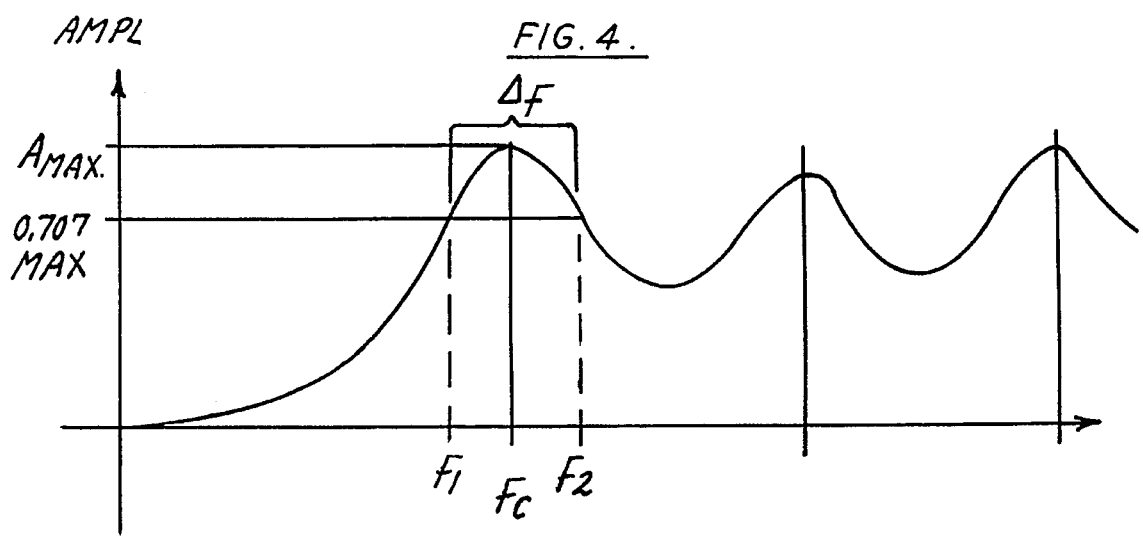
FIG. 4 is a graph of the vibrational response induced in the material using the technique of FIG. 3.

As shown in FIGS. 3 and 4, an alternate technique for measuring the damping factor and, hence, material fatigue, may be used. As before, the vibration in the part 20 is picked up by a transducer 28 for converting the sensed vibrational signals to an electrical signal which is then amplified by an amplifier 30 for input to a computer 32. However, the initial energy input to the part 20 is achieved by way of a frequency generator 40 which produces an electrical output at a particular frequency which is then amplified by a power amplifier 42 and fed to a second transducer 44, which may be a speaker or shaker or other such device, which is coupled to the part 20. The frequency generator 40 is then tuned to frequencies sweeping through the range of the lowest natural frequencies of the part 20 to thereby produce a continuous vibrational response therein as shown in FIG. 4. A peak amplitude $F_c$ of one of the several natural harmonics induced in the part 20 is chosen for measurement of the damping factor. As is well known in the art, the damping factor is equal to the half power bandwidth $\Delta F$, or F2—F1, divided by the center frequency Ft. F1 and F2, the half power frequencies, are those frequencies at which the amplitude is 0.707 times the maximum amplitude. As shown in FIG. 3, the existence of a crack 46 would affect the vibrational response of the part 20 and, hence, the damping factor measured with the inventor's technique, thereby becoming detected for suitable correction thereto.

Either or both of these techniques may be conveniently used to determine the damping factor of a particular part. The damping factor may be periodically measured for a particular part to develop a history thereof and thereby be used to monitor the developing fatigue in the part as an aid to deciding when it should be replaced or repaired. Alternately, the damping factor measured by the techniques disclosed and claimed herein could be used by comparing them with standardized damping factors for similar kinds of metals and parts.

In the preferred embodiment, and as shown in the drawings, stand alone personal computers are depicted. However, as is well known to those of ordinary skill in the art, portable PC's are well known and readily available commercially such that a suitable device for portable use and application could readily be achieved. Furthermore, although the inventor has not developed any such device, a custom made "damping factor detector" could readily be designed utilizing only those computer elements required including, e.g., a computer chip, a custom readout, and keyboard or other data entry means. Additionally, hard copy readout could readily be provided. It is intended that all of these alternatives be included within the scope of the present invention.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A method for determining a level of fatigue of a material, the method comprising the steps of:

inducing a vibration in the material by continuously exciting said material with a continuous stream of energy oscillating at an input frequency substantially equal to a natural frequency of said material;

measuring a dynamic response of the material to the induced vibration;

determining a damping factor of the material from the measured response; and comparing the damping factor with at least one predetermined damping factor to determine the level of fatigue of the material.

2. The method of claim 1 wherein the step of continuously exciting said material includes the step of varying the input frequency of said energy stream to thereby match said input frequency to the natural frequency.

3. The method of claim 2 wherein the step of determining the damping factor includes the steps of:

determining the natural frequency of said material;

determining a half-power bandwidth of said response at said natural frequency; and comparing the half-power bandwidth with the natural frequency to thereby determine the damping factor.

4. The method of claim 3 wherein the step of measuring includes the steps of:

coupling a transducer to said material;

inputting the output of said transducer to a computer; and wherein the step of comparing the half-power bandwidth with the natural frequency includes the step of using the computer.

5. The method of claim 3 wherein the step of determining the half-power bandwidth of the response includes the steps of:

measuring an amplitude of the response at the natural frequency;

varying the input frequency of said energy stream to thereby vary the amplitude of the response;

determining two half-power frequencies at which the varied amplitude is approximately 0.707 times as great as the amplitude of the response at the natural frequency;

determining a range between the two half-power frequencies; and dividing the range between the two half-power frequencies by the natural frequency.

6. A device for determining a level of fatigue of a material, the device comprising a vibrator for inducing a vibration in the material, a transducer for coupling to the material, the transducer being configured to measure a vibrational response of the material, and a programmed electronic machine connected to the transducer, the machine being configured to calculate a damping factor of the material from the measured vibrational response, the damping factor being representative of the level of fatigue thereof, wherein the vibrator is configured to introduce a continuous stream of energy to said material at an input frequency substantially equal to a natural frequency of the material.

7. The device of claim 6 wherein said vibrator comprises a frequency generator whose output is connected to a speaker, said speaker being coupled to said material.

8. The device of claim 7 wherein said vibrator further comprises an amplifier connected between said frequency generator and said speaker.

9. A method for determining a level of fatigue of a material, the method comprising the steps of:

exciting said material with a continuous stream of energy oscillating over a plurality of input frequencies within a range of frequencies surrounding a natural frequency of said material;

measuring an amplitude of a response from said material at each of said plurality of input frequencies;

determining a damping factor of said material from the measured amplitude of the material response; and determining the level of fatigue of the material from the determined damping factor.

10. The method of claim 9 wherein the step of determining the level of fatigue of the material from the determined damping factor comprises the step of comparing the determined damping factor with at least one predetermined damping factor to determine the level of fatigue of the material.

11. The method of claim 10 wherein the step of comparing the determined damping factor with at least one predetermined damping factor includes the step of identifying a reduction in the determined damping factor when compared to the at least one predetermined damping factor.

12. The method of claim 10 wherein the at least one predetermined damping factor is taken from historical data for the same material.

13. The method of claim 10 wherein the at least one predetermined damping factor is taken from generalized data from a group of materials which are similar to the material being analyzed.

14. The method of claim 9 wherein the determined damping factor comprises a first damping factor, the method further comprising the steps of:

waiting for a period of time; and repeating the steps of exciting said material with the continuous stream of energy oscillating over the plurality of input frequencies within the range of frequencies surrounding the natural frequency of said material, measuring the amplitude of the response from said material at each of said plurality of input frequencies, and determining a second damping factor of said material from the measured amplitude of the material response; and wherein the step of determining the level of fatigue of the material from the determined damping factor comprises the step of comparing the second damping factor with the first damping factor to determine the level of fatigue of the material.

15. The method of claim 9 wherein the step of determining the damping factor includes the steps of:

determining a half-power bandwidth of said response at said natural frequency; and dividing the half-power bandwidth by the natural frequency to thereby determine the damping factor.

16. The method of claim 9 wherein the step of determining the damping factor includes the steps of:

estimating a center frequency of said response;

estimating a half-power bandwidth of said response; and dividing the half-power bandwidth by the center frequency to thereby determine an estimation of the damping factor.

17. The method of claim 9 wherein each of the steps is performed on a material comprised of a plurality of components joined together.

18. The method of claim 9 wherein each of the steps is performed on a material comprised of a single component.

* * * * *